US005472983A

United States Patent [19]
Flitter et al.

[11] Patent Number: 5,472,983
[45] Date of Patent: Dec. 5, 1995

[54] BENZAMIDE-CONTAINING PHARMACEUTICAL COMPOSITIONS

[75] Inventors: William D. Flitter, Mountain View; Kirk R. Maples, San Jose; Richard E. Paylor; Helming Tan, both of Sunnyvale; Allan L. Wilcox, Fremont, all of Calif.

[73] Assignee: Centaur Pharmaceuticals, Inc., Sunnyvale, Calif.

[21] Appl. No.: 227,777

[22] Filed: Apr. 14, 1994

[51] Int. Cl.$^6$ .................... A61K 31/16; A61K 31/165
[52] U.S. Cl. .................... 514/599; 514/617; 514/619; 514/629
[58] Field of Search .................... 514/617, 599, 514/619, 629

[56] References Cited

U.S. PATENT DOCUMENTS

| | | | |
|---|---|---|---|
| 3,883,590 | 5/1975 | Schmerling | 260/558 R |
| 4,994,460 | 2/1991 | Dextraze et al. | 514/252 |

FOREIGN PATENT DOCUMENTS

| | | |
|---|---|---|
| 0232199 | 8/1987 | European Pat. Off. . |

OTHER PUBLICATIONS

Banasik et al., "Specific inhibitors of poly (ADP–Ribose) synthetase and mono(ADP–ribosyl) transferase" *J. Biol. Chem.* (1992) 267:1569–1575.

Bishop et al., "Synthesis and in vitro evaluation of 2,3-dimethoxy-5-(fluoroalkyl-substituted benzamides: high–affinity ligands for CNS dopamine $D_2$ receptors" *J. Med. Chem.* (1991) 34:1612–1624.

Burns, R. S., et al., in "A Primate Model of Parkinsonism . . . " *Proc. Natl. Acad. Sci USA* (1983) 4546–4550.

Communications to the Editor, "Evolution of a Novel Series of [(N,N-Dimethylamino)propyl]-and Piperazinylbenzanilides as the First Selective $5-HT_{1D}$ Antagonists[1]" *Journal of Medical Chemistry* (1994) 37:15, 2253–2255.

El Tayar et al., "Interaction of neuroleptic drugs with rat striatal D–1 and D–2 dopamine receptors: a quantitative structure—affinity relationship study" *Eur. J. Med. Chem.* (1988) 23:173–182.

Gerlach, M. et al., "MPTP Mechanisms of Neurotoxicity and the Implications for Parkinson's Disease" *European Journal of Pharmacology* (1991) 273–386.

Heikkila, R. E., et al., in "Dopaminergic Neurotoxicity of 1–Methyl–4–Phenyl–1,2,5,6–Tetrahydropyridine in Mice" *Science* (Jun. 29, 1984) 224:1451–1453.

Högberg et al., "Potential antipsychotic agents. 9. Synthesis and stereoselective dopamine D–2 receptor blockade of a potent class of substituted (R)-N-[benzyl-2-pyrrolidinyl)methyl] benzamides. Relations to other side chain congeners" *J. Med. Chem.* (1991) 34:948–955.

Katopodis et al., "Novel substrates and inhibitors of peptidylglycine α–amidating monooxygenase" *Biochemistry* (1990) 29:4541–4548.

Langston J. W. et al., in "Chronic Parkinsonism in Humans Due to a Product of Meperidine–Analog Synthesis" *Science* (Feb. 25, 1983), 219, 979–980.

Marsden, C. D., "Review Article—Parkinson's Disease" *Lancet* (Apr. 21, 1990) 948–952.

Monković et al., "Potential non–dopaminergic gastrointestinal prokinetic agents in the series of substituted benzamides" *Eur. J. Med. Chem.* (1989) 24:233–240.

Rainnie et al., "Adenosine inhibition of mesopontine cholinergic neurons: implications for EEG arousal" *Science* (1994) 263:689–690.

Singer, T. P., et al., "Biochemical Events in the Development of Parkinsonism . . . " *J. Neurochem.* (1987) 1–8.

*Primary Examiner*—Raymond Henley, III
*Assistant Examiner*—Phyllis G. Spivack
*Attorney, Agent, or Firm*—Burns, Doane, Swecker & Mathis

[57] ABSTRACT

A group of benzamide compounds are disclosed that are formed into pharmaceutical compositions for oral or intravenous administration to patients suffering from neurodegenerative conditions associated with dopamine depletion.

19 Claims, No Drawings

BENZAMIDE-CONTAINING PHARMACEUTICAL COMPOSITIONS

FIELD OF THE INVENTION

This invention concerns benzamide-containing pharmaceutical compositions and their use to treat or protect against neurodegenerative conditions.

BACKGROUND INFORMATION

Neurodegenerative disease encompasses a range of seriously debilitating conditions including Parkinson's disease, ALS ("Lou Gehrig's disease"), multiple sclerosis, Huntington's disease, Alzheimer's disease and the like. These conditions are characterized by a gradual but relentless worsening of the patient's condition over time. The mechanisms and causes of these diseases are becoming better understood and a variety of treatments have been suggested.

A recent summary of the state of understanding of Parkinson's disease is provided by Marsden, C. D., in "Review Article—Parkinson's Disease" Lancet (Apr. 21, 1990) 948-952. As that review points out, dopamine deficiency was identified as a key characteristic of Parkinson's disease, and the destruction of the dopaminergic nigrostriatal pathway paralleled dopamine depletion in Parkinson's patients.

Rapid development of Parkinson's-like symptoms in a small population of illicit drug users in the San Jose, California area was linked to trace amounts of a toxic impurity in the home-synthesized drugs. Subsequent studies in animal models, including monkeys, demonstrated that 1-methyl-4-phenyl-1,2,5,6-tetrahydropyridine (MPTP) was the cause of the Parkinson's-like symptoms which developed in the illicit drug users, as reported by J. W. Langston et al., in "Chronic Parkinsonism in Humans Due to a Product of Meperidine-Analog Synthesis" *Science* (Feb. 25, 1983) 219, 979–980. These early findings and the many studies that they stimulated led to the development of reliable models for Parkinson's disease, as reported by Heikkila, R. E., et al., in "Dopaminergic Neurotoxicity of 1-Methyl-4-Phenyl-1,2,5,6-Tetrahydropyridine in Mice" *Science* (Jun. 29, 1984) 224:1451–1453; Burns, R. S., et al., in "A Primate Model of Parkinsonism . . . " *Proc. Natl. Acad. Sci USA* (1983) 4546–4550; Singer, T. P., et al., "Biochemical Events in the Development of Parkinsonism . . . " *J. Neurochem.* (1987) 1–8; and Gerlach, M. et al., "MPTP Mechanisms of Neurotoxicity and the Implications for Parkinson's Disease" *European Journal of Pharmacology* (1991) 273–286. These references and others describe studies to help explain the mechanism of how the administration of MPTP to animals gives rise to motor defects characteristic of Parkinson's disease. They clearly indicate that MPTP was the cause of the Parkinson's-like symptoms that developed in the humans that had used the tainted illicit drugs and that similar motor deficits were found in other primates and other test animals which had been dosed directly with MPTP. They further point out that the administration of MPTP induces a marked reduction in the concentration of dopamine in the test subjects. Loss of dopamine in certain brain regions is well associated with Parkinson's disease.

These findings have led to the development of an assay for anti-Parkinson's agents. In this assay, test animals are given an amount of MPTP adequate to severely depress their dopamine levels. Test compounds are administered to determine if they are capable of preventing the loss of dopamine in the test animals. To the extent that dopamine levels are retained, a compound can be considered to be an effective agent for slowing or delaying the course of Parkinson's disease.

The present invention concerns eleven benzamides and their use as active pharmaceutical agents. These benzamides, N-(carboxymethyl) 4-nitrobenzamide (CPI37), N-phenyl trimethylacetamide (CPI1009), N-isobutyl 3,5-dinitrobenzamide (CPI1064), N-tert-butyl benzamide (CPI1010), N-tert-butyl 4-nitrobenzamide (CPI1020), N-tert-butyl 4-bromobenzamide (CPI1036), N-tert-butyl 4-methylbenzamide (CPI1039), N-tert-butyl 4-cyanobenzamide (CPI1043), N-tert-butyl 3,5-dinitrobenzamide (CPI1049), N-tert-butyl-N-methyl 4-nitrobenzamide (CPI1052), and N-tert-butyl 4-nitrobenzthioamide (CPI1057), are known chemical compounds. They are depicted structurally in Table 1. In this table and elsewhere in this specification, the various benzamides are accompanied by internal compound designation numbers. These numbers are provided to help keep straight the identities of these several closely related materials. *Chemical Abstracts* or *Beilstein Registry* identification numbers are also provided in Table 1.

TABLE 1

| Int. Ident. No. | Structure | Chem. Abstract No. |
|---|---|---|
| 1010 | Ph—C(=O)—NH—C(CH$_3$)$_3$ | 5894-65-5 |
| 1020 | O$_2$N—Ph—C(=O)—NH—C(CH$_3$)$_3$ | 42498-30-6 |
| 1043 | NC—Ph—C(=O)—NH—C(CH$_3$)$_3$ | Beilstein Reg. No. 3250293 |
| 1036 | Br—Ph—C(=O)—NH—C(CH$_3$)$_3$ | 42498-38-4 |
| 37 | O$_2$N—Ph—C(=O)—NH—CH$_2$COOH | 2645-07-0 |
| 1052 | O$_2$N—Ph—C(=O)—N(CH$_3$)—C(CH$_3$)$_3$ | 54284-31-0 |
| 1057 | O$_2$N—Ph—C(=S)—NH—C(CH$_3$)$_3$ | 34496-27-0 |
| 1009 | Ph—NH—C(=O)—C(CH$_3$)$_3$ | 6625-74-7 |

TABLE 1-continued

| Int. Ident. No. | Structure | Chem. Abstract No. |
|---|---|---|
| 1049 | O₂N-C₆H₃(NO₂)-C(O)-NH-C(CH₃)₃ | 56808-99-2 |
| 1064 | O₂N-C₆H₃(NO₂)-C(O)-NH-CH₂-CH(CH₃)₂ | |
| 1039 | H₃C-C₆H₄-C(O)-NH-C(CH₃)₃ | 42498-32-8 |

While these compounds are known, their utility heretofore has generally been as intermediates in chemical syntheses or in fields unrelated to the present invention. Slight structural changes yielded large differences in efficacy and toxicity. The vast majority of benzamide compounds tested had little or no activity in our screens. However, there are reports of biological activity for other, structurally different benzamides. These reports include:

El Tayar et al., "Interaction of neuroleptic drugs with rat striatal D-1 and D-2 dopamine receptors: a quantitative structure—affinity relationship study" *Eur. J. Med. Chem*, (1988) 23:173–182;

Monković et al., "Potential non-dopaminergic gastrointestinal prokinetic agents in the series of substituted benzamides" *Eur. J. Med. Chem*. (1989) 24:233–240;

Banasik et al., "Specific inhibitors of poly(ADP-Ribose) synthetase and mono(ADP-ribosyl)transferase" *J. Biol. Chem*. (1992) 267:1569–1575;

Bishop et al., "Synthesis and in vitro evaluation of 2,3-dimethoxy-5-(fluoroalkyl)-substituted benzamides: high-affinity ligands for CNS dopamine $D_2$ receptors" *J. Med. Chem*. (1991) 34:1612–1624;

Högberg et al., "Potential antipsychotic agents. 9. Synthesis and stereoselective dopamine D-2 receptor blockade of a potent class of substituted (R)-N-[benzyl-2-pyrrolidinyl)methyl]benzamides. Relations to other side chain congeners" *J. Med. Chem*. (1991) 34:948–955;

Katopodis et al., "Novel substrates and inhibitors of peptidylglycine α-amidating monooxygenase" *Biochemistry* (1990) 29:4541–4548; and Rainnie et al., "Adenosine inhibition of mesopontine cholinergic neurons: implications for EEG arousal" *Science* (1994) 257:689–690.

STATEMENT OF THE INVENTION

It has now been found that a family of eleven benzamide compounds exhibit strong activity against Parkinson's disease as measured by their ability to prevent MPTP-induced reduction of dopamine levels. These eleven compounds are:

N-(carboxymethyl) 4-nitrobenzamide,
N-phenyl trimethylacetamide,
N-isobutyl 3,5-dinitrobenzamide,
N-tert-butyl benzamide,
N-tert-butyl 4-nitrobenzamide,
N-tert-butyl 4-bromobenzamide,
N-tert-butyl 4-methylbenzamide,
N-tert-butyl 4-cyanobenzamide,
N-tert-butyl 3,5-dinitrobenzamide,
N-tert-butyl-N-methyl 4-nitrobenzamide, and
N-tert-butyl 4-nitrobenzthioamide.

The first of these compounds has an acid functionality which can be present as such or as a pharmaceutically acceptable salt. When this "compound" is referred to it is to be understood that these salts are included, as well.

The activity demonstrated by these compounds is unexpected and not predictable based on the fact that other, structurally closely related materials lack the activity.

The invention can take the form of pharmaceutical compositions based on one or more of these compounds. It can also take the form of methods of treating neuordegenerative conditions.

Thus, in one aspect this invention provides pharmaceutical compositions which include one or more of the following benzamide compounds:

N-(carboxymethyl) 4-nitrobenzamide,
N-phenyl trimethylacetamide,
N-isobutyl 3,5-dinitrobenzamide,
N-tert-butyl benzamide,
N-tert-butyl 4-nitrobenzamide,
N-tert-butyl 4-bromobenzamide,
N-tert-butyl 4-methylbenzamide,
N-tert-butyl 4-cyanobenzamide,
N-tert-butyl 3,5-dinitrobenzamide,
N-tert-butyl-N-methyl 4-nitrobenzamide, and
N-tert-butyl 4-nitrobenzthioamide in a pharmaceutically acceptable carrier. This carrier is preferably an oral carrier but can be an injectable carrier as well. These pharmaceutical compositions can be in bulk form but more typically are presented in unit dosage form.

In another aspect this invention provides a method for treating a patient suffering from a neurodegenerative condition. This method involves administering to the patient an effective neurodegenerative condition-treating amount of one or more of the pharmaceutical compositions just described.

In another aspect this invention provides a method for treating a patient suffering from a condition characterized by progressive loss of central nervous system function. This method involves administering to the patient with loss of central nervous system function an effective amount of the pharmaceutical composition of one or more of the pharmaceutical compositions just described.

In a most important aspect this invention provides a method for treating a patient suffering from a progressive loss of central nervous system function associated with Parkinson's disease. This method involves administering (preferably orally) to the patient with loss of progressive central nervous system function an effective amount of one or more of the pharmaceutical compositions just described.

DETAILED DESCRIPTION OF THE INVENTION

The Compounds

The pharmaceutical compositions of this invention employ one or more of the eleven benzamide compounds set forth in the Statement Of the Invention as active agents. While any of the eleven materials can be used alone or as mixtures, based on their relatively higher activity, N-tert-butyl benzamide (CPI1010), N-tert-butyl 4-nitrobenzamide (CPI1020), N-tert-butyl 3,5-dinitrobenzamide (CPI1049), N-tert-butyl 4-nitrobenzthioamide (CPI1057), and N-isobutyl 3,5-dinitrobenzamide (CPI1064) are preferred.

Of these, N-tert-butyl benzamide (CPI1010) and

N-tert-butyl 4-nitrobenzamide (CPI1020)

are more preferred, with N-tert-butyl 4-nitrobenzamide (CPI1020) being the most preferred at this time.

If compound CPI37 is employed it can be used as a salt in which the carboxylic acid hydrogen is replaced with a pharmaceutically acceptable cation. Most commonly, this cation is a monovalent material such as sodium, potassium or ammonium, but it can also be a multivalent cation in combination with a pharmaceutically acceptable monovalent anion, for example calcium with a chloride, bromide, iodide, hydroxyl, nitrate, sulfonate, methane sulfonic acid, acetate, tartrate, oxalate, succinate, palmoate or the like anion; magnesium with such anions; zinc with such anions or the like.

Among these materials, the free acid and the simple sodium, potassium or ammonium salts are most preferred with the calcium and magnesium salts also being preferred but somewhat less so.

Pharmaceutical Compositions

The benzamide compounds are formulated into pharmaceutical compositions suitable for oral or other appropriate routes of administration.

The compositions for oral administration can take the form of bulk liquid solutions or suspensions, or bulk powders. More commonly, however, the compositions are presented in a unit dosage form to facilitate accurate dosing. Typical unit dosage forms include prefilled, premeasured ampules or syringes of the liquid compositions or pills, tablets, capsules or the like in the case of solid compositions. In such compositions, the benzamide compound is usually a minor component (0.1 to say 50% by weight or preferably from about 1 to about 40% by weight) with the remainder being various vehicles or carriers and processing aids helpful for forming the desired dosing form. A liquid form may include a suitable aqueous or nonaqueous vehicle with buffers, suspending dispensing agents, colorants, flavors and the like.

A solid form may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

In the case of injectable compositions, they are commonly based upon injectable sterile saline or phosphate-buffered saline or other injectable carriers known in the art. Again the active benzamide is typically a minor component, often being from about 0.05 to 10% by weight with the remainder being the injectable carrier and the like.

These components for orally administrable or injectable compositions are merely representative. Other materials as well as processing techniques and the like are set forth in Part 8 of *Remington's Pharmaceutical Sciences*, 17th edition, 1985, Mack Publishing Company, Easton, Pa., which is incorporated by reference.

One can also administer the compounds of the invention in sustained release forms or from sustained release drug delivery systems. A description of representative sustained release materials can be found in the incorporated materials in *Remington's Pharmaceutical Sciences*.

Conditions Treated and Treatment Regimens

The conditions treated with the benzamide-containing pharmaceutical compositions may be classed generally as neurodegenerative conditions. These include conditions characterized by protracted low grade stress upon the central nervous system and gradual progressive loss of central nervous system function. These conditions include Alzheimer's disease, Parkinson's disease, multiple sclerosis, Huntington's disease, amyotrophic lateral sclerosis (ALS), multi-infarct dementia, macular degeneration, retinopathy and the like. Each of these conditions is characterized by a progressive loss of function. The benzamide compound-containing pharmaceutical compositions of this invention, when administered orally or by injection such as intravenously, can slow and delay and possibly even to some extent reverse the loss of function.

Injection dose levels for treating these conditions range from about 0.1 mg/kg/hour to at least 10 mg/kg/hour, all for from about 1 to about 120 hours and especially 24 to 96 hours. A preloading bolus of from about 10 to about 500 mg or more may also be administered to achieve adequate steady state levels.

With these neurodegenerative conditions, the regimen for treatment usually stretches over many months or years so oral dosing is preferred for patient convenience and tolerance. With oral dosing, one to five and especially two to four and typically three oral doses per day are representative regimens. Using these dosing patterns, each dose provides from about 1 to about 15 mg/kg of benzamide, with preferred doses each providing from about 1 to about 10 mg/kg and especially about 1 to about 5 mg/kg.

Of course, one can administer the benzamide compound as the sole active agent or one can administer it in combination with other agents.

EXAMPLES

The invention will be further described by the following Examples. These are provided to illustrate several preferred embodiments of the invention but are not to be construed as limiting its scope which is, instead, defined by the appended claims. Examples 1–11 demonstrate the preparation of each of the benzamide compounds employed in the compositions and methods of this invention. Examples 12–15 demonstrate the preparation of pharmaceutical compositions based on the compounds. Thereafter biological test results illustrating the activity of the compositions of the invention are provided.

Example 1

Preparation of N-tert-butyl benzamide (CPI1010)

tert-Butyl amine (14.6 g, 0.200 mole) was stirred in ethyl acetate (150 mL, purified by washing with 5% sodium carbonate solution, saturated sodium chloride solution, drying over anhydrous magnesium sulfate, and filtering through fluted filter paper) and cooled to 5° C. with an ice bath. Benzoyl chloride (14.0 g, 0.100 mole) in purified ethyl acetate (75 mL) was added dropwise at such a rate to maintain the temperature below 10° C. The ice bath was removed upon complete addition of benzoyl chloride solution and the reaction stirred for 4 hours. The reaction mixture was then filtered on a Büchner funnel, the filtrate washed three times with 5% HCl, once with saturated sodium chloride, dried over anhydrous magnesium sulfate, filtered through fluted filter paper, and the solvent stripped off leaving white crystalline product. The product was dried in a vacuum oven at 24 mm and 45° C. for 14 hours. This procedure produced 15.46 g of crystals of the desired product N-tert-butyl benzamide (CPI1010) (87% yield), mp 133°–135° C. Proton nuclear magnetic resonance (89.55 MHz) showed absorptions at 7.75 ppm (m, 2H; 2,6-aryl H); 7.45 ppm (m, 3H; 3,4,5-aryl H); 5.97 ppm (bs, 1H; N-H); 1.471 ppm (s, 9H, tert-butyl H).

Example 2

Preparation of N-tert-butyl 4-nitrobenzamide (CPI1020)

The preparation of Example 1 was repeated with the changes that tert-butyl amine (14.6 g, 0.200 mole) and 4-nitrobenzoyl chloride (18.6 g, 0.100 mole) were the starting reactants. This reaction produced 17.13 g of crystals of the desired product (77% yield), mp 162°–163° C. proton nuclear magnetic resonance (89.55 MHz) showed absorptions at 8.257 ppm (d, 8.8 Hz, 2H; 3,5-aryl H); 7.878 ppm (d, 8.8 Hz, 2H; 2,6-aryl H); 6.097 ppm (bs, 1H; N-H); 1,500 ppm (s, 9H; tert-butyl H).

Example 3

Preparation of N-tert-butyl 4-bromobenzamide (CPI1036)

The preparation of Example 1 was repeated with the changes that tert-butyl amine (4.02 g, 0.055 mole) and 4-bromobenzoyl chloride (6.04 g, 0.0275 mole) were the starting reactants and benzene was the reaction medium. This reaction produced 6.24 g crystals (89% yield), mp 130°–133° C. Proton nuclear magnetic resonance (89.55 MHz) showed absorptions at 7.562 ppm (s, 4H; aryl H); 5.910 ppm (bs, 1H; N-H); 1.464 ppm (s, 9H; tert-butyl H).

Example 4

Preparation of N-tert-butyl 4-cyanobenzamide (CPI1043)

The preparation of Example 1 was repeated with the changes that the starting reactants were tert-butyl amine (4.38 g, 0.060 mole) and 4-cyanobenzoyl chloride (5.08 g, 0.030 mole) and the reaction was carried out in benzene to produce 5.58 g of crystals of the desired product (92% yield), mp 146°–148° C. Proton nuclear magnetic resonance (89.55 MHz) showed absorptions at 7.829 ppm (d, 8.4 Hz, 2H; 3,5-aryl H); 7.690 ppm (d, 8.4 Hz, 2H; 2,6-aryl H); 5.996 ppm (bs, 1H; N-H); 1.477 ppm (s, 9H; tert-butyl H).

Example 5

Preparation of N-tert-butyl 4-methylbenzamide (CPI1039)

The preparation of Example 1 was repeated with the changes that the starting reactants were tert-butyl amine (4.72 g, 0.065 mole) and 4-methylbenzoyl chloride (5.02 g, 0.0325 mole), the reaction was carried out in benzene and the reaction produced 5.54 g of crystals of the desired product (89% yield), mp 114°–116° C. Proton nuclear magnetic resonance (89.55 MHz) showed absorptions at 7.615 ppm (d, 8 Hz, 2H; 2,6-aryl H); 7.193 ppm (d, 8 Hz, 2H; 3,5-aryl H); 5.970 ppm (bs, 1H; N-H); 2.377 ppm (s, 3H; 4-$CH_3$); 1.461 ppm (s, 9H; tert-butyl H).

Example 6

Preparation of N-tert-butyl 3,5-diniobenzamid (CPI1049)

The preparation of Example 1 was repeated with the changes that the starting reactants were tert-butyl amine (7.3 g, 0.100 mole) and 3,5-dinitrobenzoyl chloride (7.92 g, 0.050 mole), the reaction was carried out in benzene and produced 7.24.g of crystals of the desired product (54% yield), mp 158°–159° C. Proton nuclear magnetic resonance (89.55 MHz) showed absorptions at 9.124 ppm (t, 2.2 Hz, 1H; 4-aryl H); 8.888 ppm (d, 2.2 Hz, 2H; 2,6-aryl H); 6.02 ppm (bs, 1H; N-H); 1.525 ppm (s, 9H; tert-butyl H).

Example 7

Preparation of N-tert-butyl-N-methyl 4-nitrobenzamide (CPI1052)

The preparation of Example 1 was repeated with the changes that the starting reactants were N-tert-butyl-N-methyl amine (3.36 g, 0.0386 mole) and 4-nitrobenzoyl chloride (3.58 g, 0.0193 mole), the reaction was carried out in benzene, the product was crystallized from cold ethanol, and the desired product was 3.31 g of crystals (28% yield), mp 119°–121° C. Proton nuclear magnetic resonance (89.55 MHz) showed absorptions at 8.252 ppm (d, 8.8 Hz, 2H; 3,5-aryl H); 7.569 ppm (d, 8.8 Hz, 2H; 2,6-aryl H); 2.838 ppm (s, 3H; N-$CH_3$); 1.526 ppm (s, 9H; tert-butyl H).

Example 8

Preparation of N-phenyl trimethylacetamide (CPI1009)

The preparation of Example 1 was repeated with the changes that the starting reactants were aniline (24.18 g, 0.260 mole) and trimethylacetoyl chloride (15.06 g, 0.125 mole), the reaction was carried out in benzene and produced 13.24 g of crystals of the desired product (60% yield), mp 132°–132.5° C. Proton nuclear magnetic resonance (89.55 MHz) showed absorptions at 7.568–7.078 ppm (m, 5H; aryl H); 1.310 ppm (s, 9H; tert-butyl H).

Example 9

Preparation of N-tert-butyl 4-nitrobenzthioamide (CPI1057)

The preparation of Example 1 was repeated with the changes that N-tert-butyl 4-nitrobenzamide (3.00 g, 0.0135 mole) and 2,4-bis (4-methoxyphenyl) -1,3 -dithia-2,4- diphosphetane-2,4-disulfide (3.28 g, 0.0081 mole) were the starting reactants and the reaction was carried out by refluxing in 50 mL dry toluene solvent for 3 hours. In addition, the solvent was removed in vacuo leaving a yellow viscous oil. The oil was taken up into ethyl acetate and the solution filtered through silica gel. The solvent was removed in vacuo, the residue taken up into ethanol, and the mixture filtered through fluted filter paper. Recrystallization from ethanol produced 2.20 g golden crystals of the desired product (68% yield), mp 136°–138° C. Proton nuclear magnetic resonance (89.55 MHz) showed absorptions at 8.21 ppm (d, 8.0 Hz, 2H; 3,5-aryl H); 7.76 ppm (d, 8.0 Hz, 2H; 2,6-aryl H); 1.67 ppm (s, 9H; tert-butyl H).

Example 10

N-(carboxymethyl) 4-nitrobenzamide (CPI37)

This compound was purchased from Aldrich Chemical Company.

Example 11

N-isobutyl 3.5-dinitrobenzamide (CPI1064)

The general procedure was used with isobutyl amine (14.6 g, 0.200 mole) and 3,5-dinitrobenzoyl chloride (23.0 g, 0.100 mole) in ethyl acetate. Produced 7.28 g (26%) crystals, mp 149°–155° C. Proton NMR (90 MHz) shows resonances at 9.168 ppm (m, 1H; 4-aryl H); 8.955 ppm (d, 2 Hz, 2H; 2,6-aryl H's); 6.526 ppm (bs, 1H; N-H); 3.378 ppm (t, 6.4 Hz, 2H; N-CH$_2$); 2.050 ppm (sep, 7 Hz, 1H; CH); 1.021 ppm (d, 6.2 Hz, 6H; CH$_3$).

Example 12

Preparation of Pharmaceutical Compositions

The compound of Example 1 is admixed as a dry powder with a dry gelatin binder in a 1:2 weight ratio. A minor amount of magnesium stearate is added as a lubricant. The mixture is formed into 250 mg tablets (80–90 mg of active benzamide) in a tablet press. If these tablets were administered to a patient suffering from a neurodegenerative condition on a thrice daily regimen they would slow the progress of the patient's disease.

Example 13

The compound of Example 2 is admixed as a dry powder with a starch diluent in a 1:1 weight ratio. The mixture is filled into 250 mg capsules (125 mg of active benzamide). If these capsules were administered to a patient suffering from a neurodegenerative condition on a twice daily or thrice daily regimen they would slow the progress of the patient's disease.

Example 14

The compound of Example 3 is suspended in a sweetened flavored aqueous medium to a concentration of 50 mg/cc. If 5 ccs of this liquid material was administered to a patient suffering from a neurodegenerative condition such as Parkinson's disease on a twice daily or thrice daily regimen they would slow the progress of the patient's loss of function brought about by the disease.

Example 15

The compound of Example 4 is dissolved in a buffered sterile saline injectable aqueous medium to a concentration of 10 mg/cc. If 50 ccs of this liquid material was administered to a patient suffering from a neurodegenerative condition such as Parkinson's disease on a daily regimen this dose would slow the progress of the patient's loss of function brought about by the disease.

It will be appreciated that any of the eleven compounds could be employed on any of these representative formulations, and that any of these formulations could be administered in any of these manners so as to treat any of the neurodegenerative conditions described in this specification. Parkinson's Disease Screening Methods Dopamine Depletion Studies.

C57BL/6J mice were pretreated with either saline or a drug (100 mg/kg, i.p.) 30 min before MPTP. MPTP was dissolved in saline and given subcutaneously as a single dose of 30 mg free base/kg body weight to produce an 80% reduction in striatal dopamine. Insoluble drugs were dissolved or suspended in 10% hydroxypropyl-β-cyclodextrin in saline. Groups of mice (n=6 per group) received either vehicle plus saline, vehicle plus MPTP, drug plus saline, or drug plus MPTP. Mice received additional doses of drug (same concentration and route as before) 24 and 48 hours after initial treatment. Seventy two hours after receiving MPTP, mice were sacrificed using cervical dislocation and the striata were excised. The tissue was homogenized in 0.4N perchloric acid, centrifuged, and the supernatant analyzed by high performance liquid chromatography/electrochemical detection (HPLC/ED) for dopamine levels. Supernatants were stored in a –90° C. freezer between the time of collection and analysis.

Selected drugs were also tested orally using analogous procedures to those described above. Instead of dissolving the drug in saline or hydroxypropyl-β-cyclodextrin, the drugs were combined with an equivalent amount of methyl cellulose and were homogenized in water. The dosage amount (100 mg/kg) and all other experimental parameters were the same as before.

The results of these experiments are provided in Table 2. These results show that the compositions of this invention were effective in preventing dopamine depletion following MPTP challenge. For comparison purposes the same tests were run on compositions based on closely related benzamide compounds and little or no activity was found.
Dopamine Depletion and Monoamine Oxidase Inhibition Studies Further confirming experiments were also performed on several of the compositions of the invention. These experiments were designed to confirm the initial results and to assess the effect of the drugs on the activity of striatal monoamine oxidase in young (60–70 days old) C57BL/6 mice. Two studies were performed for each drug: 1) Dopamine and dopamine metabolites were determined in striatal tissues six days after MPTP, and 2) MPTP to MPP$^+$ ratios in striatal tissues were determined exactly two hours after MPTP dosing. This ratio of parent compound to metabolite was used as a marker for monoamine oxidase activity.

The experimental design was as follows:

| Treatment | N |
| --- | --- |
| Vehicle (i.p.) + Saline (s.c.) | 10 |

| Treatment | N |
| --- | --- |
| Drug (i.p.) + Saline (s.c.) | 10 |
| Vehicle (i.p.) + MPTP (s.c.) | 10 |
| Drug (i.p.) + MPTP (s.c.) | 10 |

For dopamine studies, drugs were administered as a single dose of 100 mg/kg (i.p., dissolved in saline or 10% hydroxypropyl-β-cyclodextrin in saline) 30 min before MPTP treatment and 24 and 48 hr after. MPTP (as a solution of its hydrochloride salt) was administered as a single subcutaneous injection of 40 mg/kg (calculated as the free base). Animals (n=5) were sacrificed six days after drug administration, the brain removed and striata dissected and immediately frozen in liquid nitrogen. Striatal dopamine and dopamine metabolites were assayed using HPLC/ED. For MPTP/MPP$^+$ studies, mice (n=5) were sacrificed two hours after drug administration and striatal tissue was excised and stored as described above. MPTP and drug administration was identical to that used for the dopamine studies, except only a single drug dosing was performed. MPTP and MPP$^+$ concentrations were determined using gas chromatography/mass spectroscopy (GC/MS) isotope dilution assay methods.

Data were analyzed for statistical significance using ANOVA followed by comparison of groups using Student's t test and other post hoc statistical methods as needed.

TABLE 2

| Compound | In House Dopamine Depletion i.p. Percent of Control[a] | In House Dopamine Depletion Oral Percent of Control[a] | Contract Dopamine Depletion i.p. Percent of Control[b] | MAO Inhibition[c] |
| --- | --- | --- | --- | --- |
| CPI-37 | 52 | 0 | — | — |
| CPI-1009 | 47 | 0 | 15 | No |
| CPI-1010 | 60 | 55 | 36 | No |
| CPI-1020 | 84 | 65 | 32 | No |
| CPI-1036 | 48 | 20 | — | — |
| CPI-1039 | 53 | 3 | — | — |
| CPI-1043 | 36 | 0 | — | — |
| CPI-1049 | 70 | 39 | — | — |
| CPI-1052 | 67 | 25 | — | — |
| CPI-1057 | 44 | 32 | — | — |
| CPI-1064 | 25 | 43 | — | — |

[a]Drug given before and after 30 mg/kg MPTP, dopamine measured 3 days later. Control mice receiving only MPTP were 80% depleted.
[b]Drug given before and after 40 mg/kg MPTP, dopamine measured 6 days later.
[c]Inhibition of monoamine oxidase (MAO), based on MPTP/MPP$^+$ ratios.

What is claimed is:

1. A pharmaceutical composition comprising a benzamide compound selected from the group consisting of N-(carboxymethyl) 4-nitrobenzamide,
N-phenyl trimethylacetamide,
N-isobutyl 3,5-dinitrobenzamide,
N-tert-butyl benzamide,
N-tert-butyl 4-nitrobenzamide,
N-tert-butyl 4-bromobenzamide,
N-tert-butyl 4-methylbenzamide,
N-tert-butyl 4-cyanobenzamide,
N-tert-butyl 3,5-dinitrobenzamide,
N-tert-butyl-N-methyl 4-nitrobenzamide, and
N-tert-butyl 4-nitrobenzthioamide in a pharmaceutically acceptable carrier.

2. The pharmaceutical composition of claim 1 wherein the carrier is an oral carrier.

3. The pharmaceutical composition of claim 2 in a unit dosage form.

4. The pharmaceutical composition of claim 1 wherein the carrier is an injectable carrier.

5. A method for treating a patient suffering from a neurodegenerative condition associated with dopamine depletion comprising administering to said patient an effective neurodegenerative condition-treating amount of the pharmaceutical composition of claim 1.

6. A method for treating a patient suffering from a progressive loss of central nervous system function associated with dopamine depletion comprising administering to said patient an effective progressive central nervous system function loss-treating amount of the pharmaceutical composition of claim 1.

7. A method for treating a patient suffering from a progressive loss of central nervous system function associated with dopamine depletion comprising orally administering to said patient an effective progressive central nervous system function loss treating amount of at least about 1 mg/kg day of benzamide compound as the pharmaceutical composition of claim 1.

8. The method of claim 7 wherein said progressive central nervous system function loss is Parkinson's disease.

9. The pharmaceutical composition of claim 1 wherein the benzamide compound is N-(carboxymethyl) 4-nitrobenzamide.

10. The pharmaceutical composition of claim 1 wherein the benzamide compound is N-phenyl trimethylacetamide, 11. The pharmaceutical composition of claim 1 wherein the benzamide compound is N-tert-butyl benzamide.

12. The pharmaceutical composition of claim 1 wherein the benzamide compound is N-tert-butyl 4-nitrobenzamide.

13. The pharmaceutical composition of claim 1 wherein the benzamide compound is N-tert-butyl 4-bromobenzamide.

14. The pharmaceutical composition of claim 1 wherein the benzamide compound is N-tert-butyl 4-methylbenzamide.

15. The pharmaceutical composition of claim 1 wherein the benzamide compound is N-tert-butyl 4-cyanobenzamide.

16. The pharmaceutical composition of claim 1 wherein the benzamide compound is N-tert-butyl 3,5-dinitrobenzamide.

17. The pharmaceutical composition of claim 1 wherein the benzamide compound is N-tert-butyl-N-methyl 4-nitrobenzamide.

18. The pharmaceutical composition of claim 1 wherein the benzamide compound is N-tert-butyl 4-nitrobenzthioamide.

19. The pharmaceutical composition of claim 1 wherein the benzamide compound is N-isobutyl 3,5-dinitrobenzamide.

* * * * *